United States Patent

Guillemaud et al.

[11] Patent Number: 5,814,817
[45] Date of Patent: Sep. 29, 1998

[54] PROCESS FOR CARRYING OUT EMISSION CARTOGRAPHY OF A BODY CORRECTED WITH RESPECT TO THE ATTENUATION BY SAID BODY

[75] Inventors: Régis Guillemaud, Gremoble; Pierre Grangeat, Saint Ismier, both of France

[73] Assignee: Commissariat A L'Energie Atomique, Paris, France

[21] Appl. No.: 642,432

[22] Filed: May 3, 1996

[30] Foreign Application Priority Data

May 4, 1995 [FR] France .................................. 95 05342

[51] Int. Cl.⁶ .................................................. G01T 1/161
[52] U.S. Cl. ...................................... 250/363.04; 250/395
[58] Field of Search ........................ 250/363.04, 363.07, 250/395

[56] References Cited

U.S. PATENT DOCUMENTS

| | | | |
|---|---|---|---|
| 4,777,367 | 10/1988 | Kawasaki et al. | 250/395 X |
| 5,155,365 | 10/1992 | Cann et al. | 250/363.04 X |
| 5,338,936 | 8/1994 | Gullberg et al. | 250/363.04 |
| 5,461,232 | 10/1995 | McCandless et al. | 250/363.04 |

FOREIGN PATENT DOCUMENTS

| | | |
|---|---|---|
| 0 145 998 | 6/1985 | European Pat. Off. . |
| 0 526 970 A2 | 2/1993 | European Pat. Off. . |
| WO 91/02265 | 2/1991 | WIPO . |
| WO 94/00779 | 1/1994 | WIPO . |

OTHER PUBLICATIONS

Bailey, D.L., et al, Journal of Nuclear Medicine 28(S), 844–851 (1987) "Improved Spect Using Simultaneous Emission and Transmission Tomography".

*Primary Examiner*—Edward J. Galick
*Attorney, Agent, or Firm*—Michael N. Meller

[57] ABSTRACT

A process provides a cartography of an emission of radiation by a body (2) that is corrected with respect to the attenuation of radiation by the body. A radiation transmissions source (3) is able to assume several positions with respect to the body and emits photons toward the body. The process includes: for each position of the radiation source, determining a transmission measurement (N) of the photons emitted by the radiation source and transmitted by the body and determining an emission measurement projection of the photons emitted by the body, the transmission measurement and the emission measurement projection being performed with the same geometry of the body. Determining, for each position of the radiation source, an attenuation correction coefficient C of radiation due to the body in order to correct the emission measurement projection (E6); and then constructing an emissions map (E2) on the basis of the attenuation-corrected, emission measurement projections.

4 Claims, 2 Drawing Sheets

PROCESS FOR CARRYING OUT EMISSION CARTOGRAPHY OF A BODY CORRECTED WITH RESPECT TO THE ATTENUATION BY SAID BODY

FIELD OF THE INVENTION

The invention relates to a process for carrying out an emission cartography or mapping of the radiation of a body, corrected with respect to the attenuation due to said body.

It can be used in all fields where it is necessary to have a real cartography of the emission of an object and particularly in the field of medical imaging, particularly for studying different cardiac disorders and in the non destructive testing field, particularly for monitoring radioactive waste.

BACKGROUND PRIOR ART

For carrying out emission cartographies of an object or body, it is known to use three-dimensional (3D) tomographic systems, also known as (3D) tomographs, making it possible to obtain two-dimensional (2D) acquisitions of measurements of radiation emitted by the object itself and measurements of radiation transmitted by an external radiation source through the object, in accordance with a succession of incidences around the object and with a random geometry.

An emission cartography provides at each point the local value of a emission activity of the radiation. The duration of the emission is dependent on the chemical nature of the emitting element. In the case of radio-active-waste, the emission decay time is generally long. In the case of medical imaging, a molecule provided with a radioactive tracer is injected into the patient and is carried by the blood to the organ to be examined. The said organ them emits photons. In this case, the emitting isotopes have a short emission period of a few hours.

FIG. 1 shows a 3D tomographic system such as is conventionally used for carrying out emission cartographies or mappings of an object and attenuation cartographies or mappings. This tomographic system 1 comprises a radiation source 3 able to supply photons to the object 2 to be studied, a collimator 5 aligned with the radiation source 3, but opposite to the object 2 and a detection means 7 is placed against the collimator 5 and which can be a gamma camera equipped with several detectors.

The radiation source 3 can assume several positions relative to the object 2 and which are located on a circular trajectory Tc. The trajectory Tc is located in a transaxial plane, which is the plane perpendicular to the rotation axis Ar. The collimator/detection means assembly is subject to the same rotary movements as the radiation source 3 on the trajectory Tc.

FIG. 1 shows the rotation axis Ar passing through the centre of the object 2, but it can also be off-centered with respect to the object 2. More specifically, the collimator 5 is generally constituted by a lead plate perforated by holes, each of which defines an acquisition cone of the radiation measured at one point of the detection means 7 and in each case having an axis defining an integral projection support or integration line. It is the collimator 5 which defines, in the tomographic system 1, the acquisition geometry of the measurements. This geometry can be a parallel geometry, conical geometry, fan geometry or any other known geometry.

The transmission source 3 can assume different forms as a function of the chosen acquisition geometry. It can be a point source located at the focal point of a conical collimator, a plane source or a line source. In the system shown in FIG. 1, as the acquisition geometry is a parallel geometry, the radiation source 3 is a plane source. For such a parallel geometry, the radiation source 3 could also be a line source having a displacement along a plane so as to simulate a transmission plane.

A tomographic system like that of FIG. 1 with a line source as the radiation source is described in an article entitled "A scanning line source for simultaneous emission and transmission measurements in SPECT" by TAN P., 1993, JNM, 34 (10), 1 752-1 760.

Such a 3D tomographic system makes it possible to implement several emission cartography production processes. The simplest standard process consists in the acquisition of emission measurement projections of radiation emitted by the object, followed by the reconstruction of the corresponding emission cartography. The 3D reconstruction of these cartographies can take place by analytical methods or iterative algebraic methods, as a function of the chosen acquisition geometry.

For a parallel or fan geometry, use is generally made of an analytical method like that using a filtering/rear projection algorithm described by F. NATERER in an article entitled "The mathematics of computerized tomography", 1986, John WILEY & Sons.

For a conical geometry, it is possible to use a direct analytical method by filtering and rear projection like that described by L. FELDKAMP, K. C. DAVID and J. W. KRESS in an article entitled "Practical cone-beam algorithm", 1984, J. Opt. Soc. Am., 1(6), 612–619.

For such a geometry, it is also possible to use a direct analytical method by rearrangement in the radon domain described by B. D. SMITH in an article entitled "Image reconstruction from cone-beam projections: necessary and sufficient conditions and reconstruction methods", IEEE Trans. on Med. Imag., MI-4(1), 14–25 and by P. GRANGEAT in EP-A-0 292 402.

No matter what the geometry chosen, iterative algebraic methods can be used. They are based on a description of the relation linking the image to be constructed with data measured by a linear equations system and a resolution of said system by iteration. For example, such a method is described by G. T. GULLBERG, G. L. ZENG, B. M. W. TSUI and J. T. HAGIUS an article entitled "An iterative reconstruction algorithm for single photon emission computed tomography with cone-beam geometry", 1989, Int., J. of Imag. Sys. and Techn., 1, 169–186.

However, such an iterative method requires a large number of calculations, so that the process is long and fastidious.

It should also be noted that when an object emits radiation, the latter is attenuated by the object, so that the cartography obtained is an attenuated emission cartography.

Processes used by the above-described tomographic system aim at correcting the emission cartography with respect to the attenuation due to the object.

One of the processes uses for the 3D reconstruction operation of the corrected emission cartography, is a uniform attenuation cartography model. Such a process is described by S. BELLINI, M. PIACENTINI, C. CAFFORIO and F. ROCCA an article entitled "Compensation of tissue absorption in emission tomography", 1979, IEEE Trans. Acoustics, Speech and Signal Processing, 27(3), 213–218. However, this process only offers a correct cartography when the attenuation map is not too complex. For example, in the medical imaging field, the attenuation card of a bust with lungs, bones and soft tissues would be much too complex to permit a good reconstruction of the corrected emission cartography. Therefore this process cannot be used in the cardiac medical imaging field.

Other processes use a real attenuation map for the 3D reconstruction of the corrected emission cartography. In addition to the emission measurement projection acquisitions, said processes consist of carrying out transmission measurement acquisitions of the radiation emitted by the 3D radiation source through the object. These acquisitions are then preprocessed so as to deduce therefrom attenuation projection measurements. These processes then consist of reconstructing the cartography of the attenuation so as to carry out, on the basis of this attenuation cartography and attenuated emission cartography, an attenuation-corrected emission cartography.

Thus, these processes use a real map of the attenuation measurements. However, such an attenuation cartography supplies attenuation coefficients defined for the energy used for the transmission measurements. It must therefore be corrected for adaptation to the energy corresponding to the radioactive element used for the emission measurements, i.e. to the radioactive element naturally occurring in the object (e.g. radioactive waste) or deliberately introduced into the object or person (particularly in medical imaging).

In such processes, the attenuation correction in the emission cartography can take place:

a) Either by means of a post-correction of the emission volume reconstructed on the basis of attenuated projections. In this case, each voxel (elementary volume) of the emission map is corrected by a coefficient linked with the mean attenuation in accordance with all the acquisition directions around the voxel. The correction can be used once only or iteratively by reconstruction-rear projection. This method is adapted to a small source located in a large attenuation volume. However, used in the opposite case, it can create an over-correction at the centre of the object. Such a correction method is described by L. T. CHANG in an article "A method for attenuation in radionuclide computed tomography", 1978, IEEE Trans. Nucl. Sci., 25(1), 198–123.

b) Or by a precorrection of emission projections by the mean attenuation calculated on the same projection beam. This method can also be used iteratively. It is adapted to an emission source having the same contours as the corresponding attenuation volume and which is also homogeneous. This method is described by A. MAZET et al an article entitled "Iterative reconstruction methods for nonuniform attenuation distribution in SPECT", 1993, JNM, 34(7), 1 204-1 209.

c) Or by an iterative calculation of the correction coefficients of the attenuation of the emission projections. On convergence, this coefficient for a pixel of the detection means is the ratio of the back projection calculated on the basis of the emission volume and the attenuated back projection calculated on the basis of the emission and attenuation volumes. Such a method is described by T. MOROZUMI, M. NAKAJIMA, K. OGAWA and S. YUTA an article entitled "Attenuation correction methods using the information of attenuation distribution for single photon emission CT", 1984, Med. Image Tech., 2, 20–28.

d) Or by a likelihood maximum iterative reconstruction method correcting the attenuation by taking it into account in estimation and back projection stages. This method, which is particularly costly in calculation time, is described in the article mentioned above by GULLBERG.

FIG. 2 is a functional diagram of two types of known processes for carrying out a corrected emission cartography or mapping. One of these processes corresponds to the path shown in dotted line form. This process consists of correcting attenuated emission projections E1 in corrected emission projections E6 on the basis of informations supplied by a real attenuation map E5 (i.e. measured), constructed by means of attenuation projections E4. This process is substantially the same as that described in the article mentioned above by MAZET.

The other process shown in FIG. 2 corresponds to the path shown in continuous line form. This process consists of constructing on the one hand an attenuated emission map E3 and on the other a map of the attenuation E5 and deducing from these two maps a corrected emission map E2. This process is substantially the same as that described by CHANG in the article mentioned above.

These two processes, as well as all the other processes based on the use of an attenuation cartography for correcting the emission cartography are difficult to implement due to the fact that the attenuation cartography is difficult to obtain.

Thus, an attenuation cartography can be calculated by means of transmission acquisitions acquired using the same gamma camera as for emission. In this specific case, the detectors of the gamma camera have an adequate size to acquire the acquisitions of the measurements in emissions, but often truncate the acquisitions of the measurements in transmission and consequently the reconstructed attenuation map has artefacts due to the truncations, which is prejudicial to the correction quality.

The attenuation cartography can also be calculated on the basis of a X scanner, which does not truncate the acquisitions of the measurements in transmission. However, in this case, the difficulty is encountered in the geometrical resetting of the transmission and emission data in the geometrical reference position, but also due to the inevitable elastic deformation of the object (or patient in the case of medical imaging) between the emission acquisitions and the transmission acquisitions.

Moreover, these methods based on attenuation cartography are expensive as regards calculating, because they require a reconstruction of the attenuation map and a reconstruction of the emission map with a generally iterative attenuation correction.

SUMMARY OF THE INVENTION

An objects of the invention aims at obviating the disadvantages of the processes referred to hereinbefore. To this end the present invention proposes a process for carrying out an attenuation-corrected emission cartography which does not require the prior production of an attenuation map.

More specifically, the invention relates to a process for carrying out a cartography of the emission of radiation by a body corrected with respect to the attenuation of radiation by said body, in which a radiation transmission source able to assume several positions with respect to the body emits photons to said body, the process comprises, for each position of the radiation source, carrying out with a detection means an acquisition of a transmission measurement of the photons emitted by the radiation source and transmitted by the body and an acquisition of an emission measurement projection of the photons emitted by the body, the transmission measurement acquisition and the acquisition of the emission measurement projection being performed with the same geometry, determining, for each position of the radiation source, the attenuation correction coefficient of the radiation due to the body in order to correct the emission measurement projection and constructing an emission map on the basis of attenuation-corrected, emission measurement projections.

According to another object of the invention, the attenuation determination comprises carrying out an acquisition of a reference transmission No obtained in the absence of the body and determining a correction coefficient C as a function of the acquisitions N and No such that Ec=Em×C, in which Em is the emission measurement projection as measured and Ec is the attenuation-corrected, emission measurement projection.

Advantagwously, the acquisition of the measurement in transmission and the acquisition of the measurement projection in emission are carried out simultaneously, the photons emitted by the radiation transmission source and the photons emitted by the body having different energies.

In an embodiment of the invention in which the body has an attenuation zone and an emission zone centred with respect to one another, the correction coefficient C is approximated by:

$$C \approx \sqrt{\frac{No}{N}}$$

in which N is the acquisition of the measurement in transmission and No the acquisition of the measurement in reference transmission.

In another embodiment of the invention, where the body has a width attenuation zone and an emission zone offcentred with respect to said attenuation zone, the correction coefficient C is approximated by:

$$C \approx \left(\frac{No}{N}\right)^{\frac{Lc}{La}}$$

in which Lc is the distance between the centre of the emission zone and the edge of the attenuation zone closest to the detection means, N is the acquisition of the measurement in transmission and No the acquisition of the measurement in reference transmission.

DETAILED DESCRIPTION OF EMBODIMENTS

The process according to the invention comprises carrying out a radiation emission cartography or mapping of an object, which is attenuation-corrected with respect to the radiation due to said object.

As a function of the field in which the process is used, the object can be a radioactive body or the body of a patient in which a radioactive element has been introduced or any other type of object able to naturally or non-naturally emit radiation. Throughout the remainder of the description reference will be made in random manner to object or body.

Figure 1:
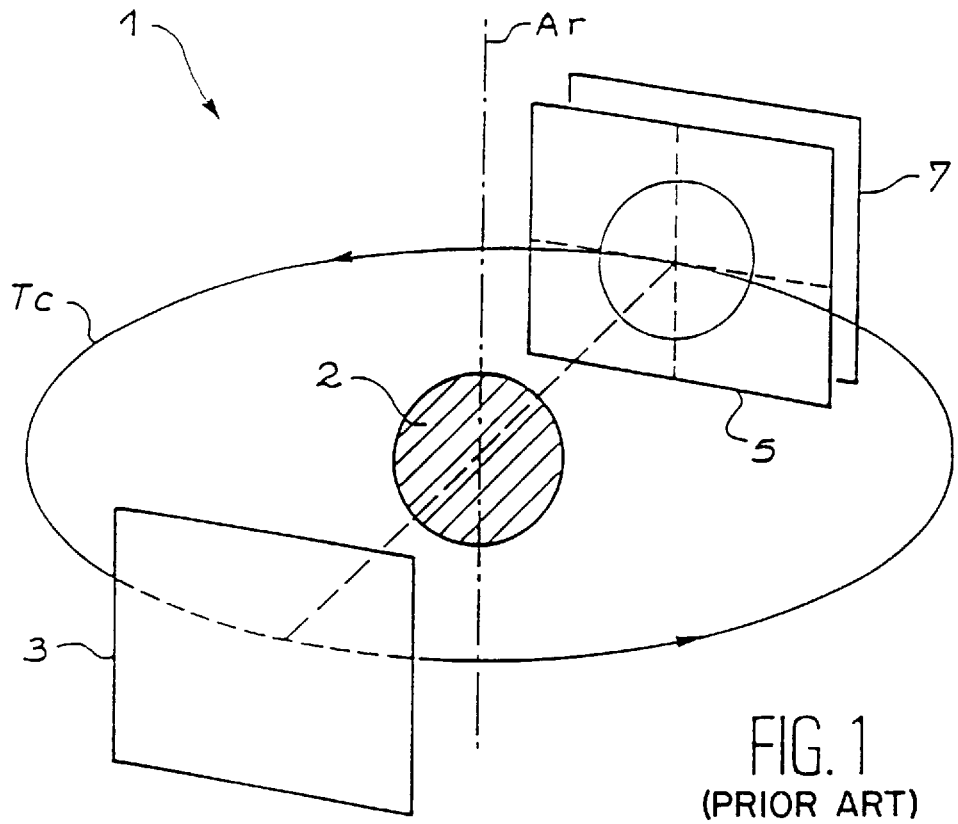
FIG. 1, already described, shows a 3D tomographic system making it possible to carry out attenuation corrected or not-corrected emission cartographies.
Figure 2:
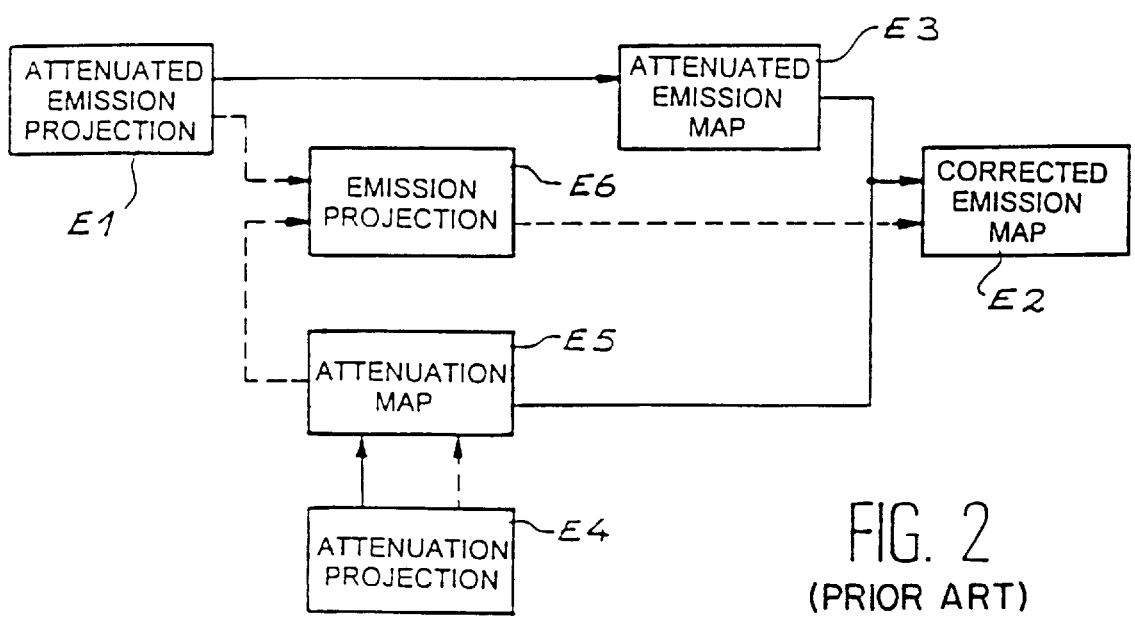
FIG. 2, already described, shows a functional diagram illustrating two known processes for carrying out attenuation-corrected emission cartographies.
Figure 3:
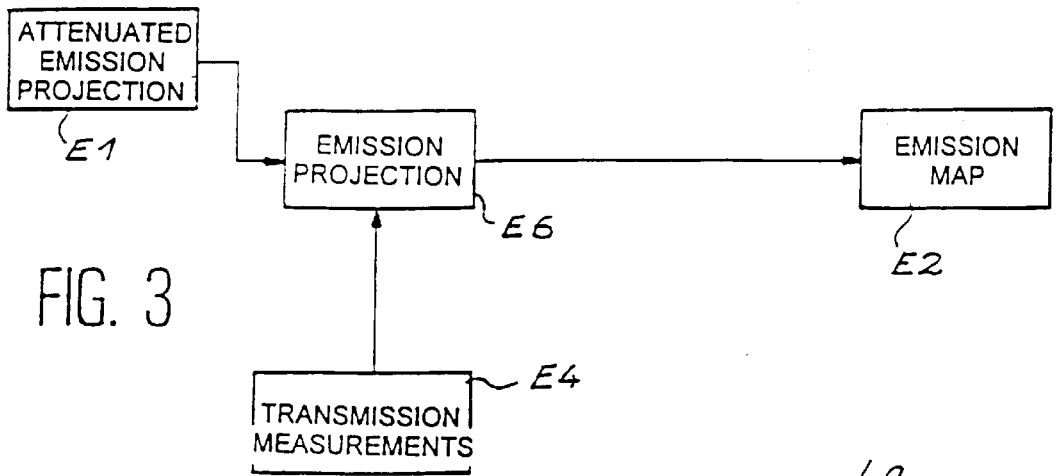
FIG. 3 is a functional diagram illustrating the process of the invention for performing an attenuation-corrected emission cartography without using an attenuation map.

FIG. 3 is a functional diagram illustrating the main stages of the process. It can be seen that the process of the invention firstly consists of carrying out the acquisition of attenuated emission measurement projections (stage E1) and in parallel transmission measurement acquisition. The transmission measurements obtained in E4 are used for correcting the attenuated emission projections of E1, so as to obtain real emission projections (stage E6). The correction emission cartography (stage E2) is then obtained by known processes based on real emission measurement projections, i.e. which are corrected, of stage E6.

According to the process of the invention, the radiation source 3 is successively placed in several positions around the body. The collimator/detection means assembly is diametrically opposite to said source 3, no matter what the position of said radiation source.

For each position of the source 3, the process consists of carrying out an acquisition of the emission measurement projection of radiation emitted by the body and a transmission measurement acquisition of radiation emitted by the source 3 through the body 2. These two acquisitions are carried out for the same geometry of the tomographic system.

The acquisitions of the measurements in emission and the acquisitions of the measurements in transmission can obviously be performed successively. However, advantageously, they are carried out simultaneously, which avoids any risk of displacement of the body between the two acquisition types. In such an embodiment, it is possible to choose as the radiation source 3 a source emitting different energy photons as compared with the photons emitted by the body. The detection means 7 is then chosen so as to be able to separate the photons emitted by the body 2 from the photons emitted by the source 3. This separation can take place either by energy difference, or by sliding interest regions on the detection means if the source 3 is moved, or by any other known means.

For example, said photon separation can take place by means of two energy windows, one of the windows being centred on the energy of the emission photons (i.e. emitted by the body 2) and the other window centred on the energy of the transmission photons (i.e. emitted by the source 3).

It is clear that a transmission measurement acquisition is a measurement of the number of photons detected on the detection means 7 after the attenuation is created by the body. This attenuation is a physical parameter associated with the materials constituting the body and the radiation source used. The attenuation measurement projection or more simply attenuation projection is the total attenuation due to the body along a chosen line.

This attenuation is determined by means of two transmission measurement acquisitions by the body (or simply transmission acquisition):

the first transmission acquisition is a reference acquisition carried out when the body is removed and is in fact a measurement acquisition of the radiation emitted by the source 3, said acquisition being designated No, the second transmission acquisition is that carried out under normal transmission conditions, as described hereinbefore and this second or measured acquisition is designated N.

The attenuation $\mu$ is then determined on the basis of the expression:

$$\frac{N}{No} = e^{-X\mu}$$

in which No is the reference transmission acquisition, N the measured transmission acquisition and $X\mu$ the integral of the attenuation $\mu$ along a chosen line.

On the basis of this attenuation $\mu$, it is possible to determine a correction coefficient C permitting the correction of emission measurement projections of the attenuation $\mu$. Thus, the corrected emission measurement projection Ec is linked with the measured emission measurement projection Em by the equation:

$$Ec = Em \times C \quad (1)$$

$$\text{with} \begin{cases} Ec = Xf \\ Em = X\mu f \end{cases} \quad (2)$$

in which Xf is the integral of the emission measurement along a line and $X\mu f$ the integral of the attenuated emission measurement along a line.

Thus, this correction coefficient C is dependent on the shape and position of the body to be studied. The equivalences have been determined for C as a function of the general shape of the body, called the emission phantom or ghost.

In the remainder of the description an explanation will be given as to how this coefficient C is determined as a function of the type of phantom corresponding to the object or body to be studied.

Figure 4A:
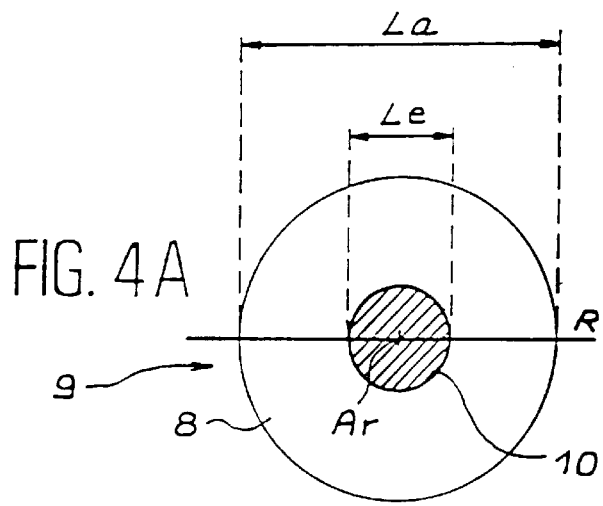
FIGS. 4A, 4B and 4C respectively shown illustrate a phantom or ghost produced by the process of the invention.

The first considered phantom is that shown in FIG. 4A. It is a phantom 9 constituted by a first or attenuation cylinder 8 with a diameter La and a second or emission cylinder 10, which has the same axis Ar as the attenuation cylinder 8, but whose diameter Le is smaller than the diameter La. For such a phantom 9, it is possible to analytically calculate the correction coefficient C in its centre for a projection beam R perpendicular to the axis of the cylinder Ar. The coefficient C is then written:

$$C = \frac{\int_{-Le/2}^{Le/2} E \cdot dl}{\int_{-Le/2}^{Le/2} E \cdot e^{-\mu(l+La/2)} \cdot dl} = \frac{\mu \cdot Le \cdot e^{\mu\frac{La}{2}}}{\left(e^{\mu\frac{Le}{2}} - e^{-\mu\frac{Le}{2}}\right)} \quad (3)$$

in which $\int E.dl$ corresponds to Xf and $\int E.e^{-\mu(l+La/2)}dl$ corresponds to $X\mu f$, in the particular case of this first phantom.

By carrying out a limited development of the difference of the exponentials $$e^{\mu\frac{La}{2}} - e^{-\mu\frac{Le}{2}}$$

and replacing in the equation (3), a correction coefficient C of order:

$$C \approx \sqrt{e^{\mu La}} \left(1 - \frac{(\mu \cdot Le)^2}{24}\right) \quad (5)$$

is obtained.

For an application to medical imaging, it is possible to use a phantom of this type, in which the diameter Le is only slightly different from the diameter La, in order to approach a cerebral acquisition configuration. Such a phantom in which the diameter Le is very small compared with the diameter La permits an approach to a cardiac acquisition configuration with a heart having a small emission compared with the trunk of the patient.

In the latter case, the correction coefficient expression C can be approximated in the same way as in the preceding case:

$$C \approx \sqrt{e^{\mu La}} \approx \sqrt{\frac{No}{N}} \quad (6)$$

Figure 4B:
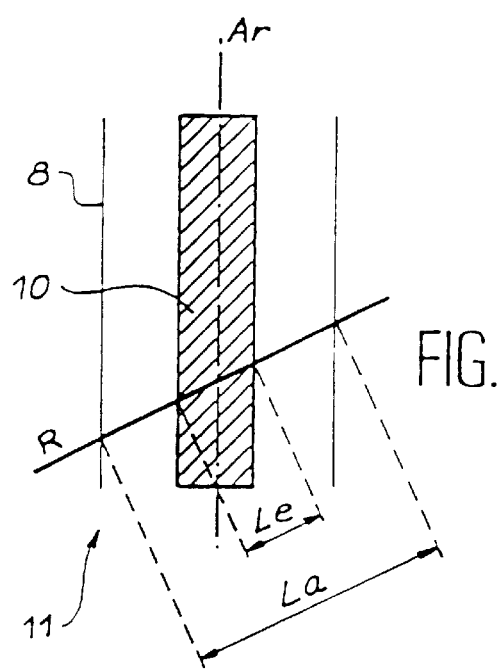

FIG. 4B shows another example of a phantom. Like the preceding phantom 9 (FIG. 4A), the phantom 11 of FIG. 4B comprises an attenuation cylinder 8 of diameter La and an emission cylinder 10 of diameter Le, which is smaller than La. For this phantom, the projection beam R also passes through the centre of the cylinders. However, this projection beam R is not perpendicular to the cylinder axis Ar. In this case and when Le <<La, the correction coefficient C is also written:

$$C \approx \sqrt{e^{\mu La}} \approx \sqrt{\frac{No}{N}} \quad (6)$$

In the same way, in the case of a phantom having the same form as the phantom 9, but for which the projection beam R does not pass through the cylinder axis Ar, the correction coefficient C would be written in the same way as in equation (6).

Thus, the correction coefficient C, as defined hereinbefore, is applicable at any point of the detection means 7. The projections of emission measurements Em can thus be corrected as follows:

$$Ec = Em \sqrt{e^{Pa}}$$

or $$Ec = Em \sqrt{\frac{No}{N}}$$

in which Ec is the attenuation-corrected, emission measurement projection and Pa the attenuation projection on the same pixel of the detection means with $Pa=\mu.La$.

Figure 4C:
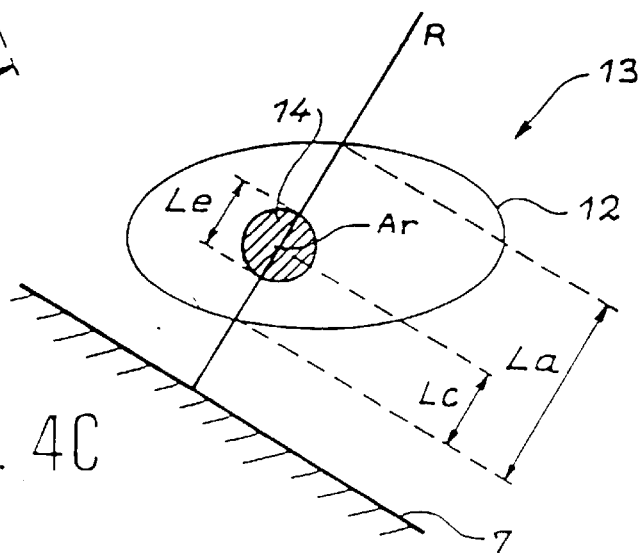

FIG. 4C shows a phantom 13 having an attenuation zone 12 and an emission zone 14 located within the attenuation zone 12, but off-centred with respect to the latter. The attenuation zone 12 has a length La, the emission zone 14 a length Le and the length along the projection beam R between the centre of the emission zone 14 and the edge of the attenuation zone 12 closest to the detection means 7 is Lc.

In this case, the correction coefficient C, for Le is much smaller than La, and would be written:

$$C \approx \left(\frac{No}{N}\right)^{\frac{Lc}{La}}$$

The corrected emission measurement projection Ec is written as a function of the emission measurement projection Em in the following way:

$$Ec = Em \, (e^{Pa})^{\frac{Lc}{La}} \quad (7)$$

or $$Ec = Em \left(\frac{No}{N}\right)^{\frac{Lc}{La}}$$

with $Pa=\mu.La$.

Thus, the emission projections are directly attenuation corrected on the basis of transmission measurements, without any reconstruction of an attenuation map being required.

This process can also be carried out by a system having, as in the prior art, a detection means 7 making it possible to acquire non-truncated emission projections. However, with this process, the transmission acquisitions can be truncated without this being prejudicial to the correction quality, because the transmission acquisition informations useful to the correction are directly deduced, the truncated informations not being useful for the correction.

According to an embodiment of the invention, use is made of a gamma camera equipped with an autocontouring system, i.e. a system making it possible to evaluate or measure the physical contour of the object or patient. This contour is then used by the gamma camera in order to turn the detection means 7 as close as possible to the object or patient without touching the latter.

For example, in cardiac imaging, it is possible to use the SOPHA-MEDICAL$^{(R)}$ gamma camera which has such an autocontouring system. In this example, a technetium 99 homogeneous plane source is positioned in alignment with the gamma camera, but opposite to the body. The source can e.g. be 60 cm from the body.

This device can be used for studying various cardiac disorders. The protocol used can be the injection of a thallium 201-labelled, pharmaceutical radioactive element. The tomographic system the carries out a three-dimensional cartography of the distribution of the tracer. In this case, the energy correction coefficient value is:

$$K=1.210.$$

In the same way as attenuation maps must be energy corrected (as explained hereinbefore) the aforementioned correction coefficients C must be corrected by a multiplication factor K, which is the ratio of the attenuation coefficient of water to the energy used for the emission measurement and the attenuation coefficient of water to the energy used for the transmission measurement, said attenuation coefficients of water being known physical quantities.

The attenuation correction proposed in this example makes it possible to study the emission map of the heart corrected with respect to artefacts and deformations created by the attenuation, so that a better diagnosis is possible. Moreover, the correction is fast and is even possible when the detector is small and only permits truncated transmission acquisitions.

We claim:

1. A process for carrying out a cartography of the emission of radiation by a body corrected with respect to the attenuation of radiation by said body, in which a radiation transmission source is capable of assuming different positions with respect to said body, by carrying out an acquisition of a reference transmission measurement No which would exist in the absence of said body, the transmission source emitting photons toward said body, the process comprising;

determining for each position of the radiation source a transmission measurement N of photons emitted by the radiation source and transmitted by said body;

determining an emission measurement projection of the photons emitted by said body, said emission measurement projection being determined with the same geometry of said body used in the transmission measurement;

obtaining for each position of the radiation source, an attentuation correction coefficient C of the radiation due to a presence of said body by the equation $$C \approx \sqrt{\frac{No}{N}}$$

where
   N is the transmission measurement;
   No is the reference transmission measurement; and
   C is the attenuation correction coefficient;

correcting the emission measurement projection for the attenuation by use of another equation $$Ec=Em \times C$$

where
   Em equals the emission measurement projection as measured;
   Ec is the attenuation corrected emission measurement projection and
   C is the attenuation correction coefficient; and constructing an emissions map on the basis of the attenuation corrected emission measurement projection.

2. Process according to claim 1, characterized in that the transmission measurement and the emission measurement projection are performed simultaneously, the photons emitted by the radiation transmission source and the photons emitted by the body having different energies.

3. A process according to claim 1, further comprising the additional step of correcting the attenuation correction coefficient C by a multiplication factor k which is a ratio of the attenuation coefficient of water for the energy used for the emission measurement to the attenuation coefficient of water for the energy used for determining the transmission measurement.

4. A process for carrying out a cartography of the emission of radiation by a body corrected with respect to the attenuation of radiation by said body, in which a radiation detection means and a radiation transmission source are capable of assuming different positions with respect to said body, by carrying out an acquisition of a reference transmission measurement No which would exist in the absence of said body, the transmission source emitting photons toward said body, and wherein the body is modeled by an attention zone and an emission zone off-center with respect to said attenuation zone, the process comprising:

determining for each position of the radiation source a transmission measurement N of photons emitted by the radiation source and transmitted by said body:

determining an emission measurement projection of the photons emitted by said body, said emission measured projection being determined with the same geometry of said body used in the transmission measurement;

obtaining for each position of the radiation source, an attenuation correction coefficient C of the radiation due to a resent of said body by the equation:

$$C \approx \left(\frac{No}{N}\right)^{\frac{Lc}{La}}$$

where
   N is the transmission measurement;
   No is the reference transmission measurement;
   C is the attenuation correction coefficient;
   La is the width of said attenuation zone; and
   Lc is the distance between the center of said emission zone and the edge of the attenuation zone closest to said detection means;

correcting the emission measurement projection for the attenuation by use of another equation $$Ec = Em \times C$$

where

Em equals the emission measurement projection as measured;

Ec is the attenuatation corrected emission measurement projection; and

C is the attenuation correction coefficient; and constructing an emissions map on the basis of the attenuation corrected emission measurement projection.

\* \* \* \* \*